(12) United States Patent
Deguchi et al.

(10) Patent No.: US 7,829,845 B2
(45) Date of Patent: Nov. 9, 2010

(54) METHODS AND INSTRUMENTS FOR IDENTIFICATION OF GLYCOSYLATED PROTEINS AND PEPTIDES

(75) Inventors: Kisaburo Deguchi, Sapporo (JP); Atsumu Hirabayashi, Kodaira (JP); Hiroki Ito, Matsudo (JP); Takashi Baba, Kawagoe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 290 days.

(21) Appl. No.: 11/878,241

(22) Filed: Jul. 23, 2007

(65) Prior Publication Data

US 2008/0048110 A1  Feb. 28, 2008

(30) Foreign Application Priority Data

Aug. 22, 2006  (JP)  ............................. 2006-225715

(51) Int. Cl.
*H01J 49/42* (2006.01)
*H01J 49/04* (2006.01)

(52) U.S. Cl. .................. 250/288; 250/282; 250/292; 250/293

(58) Field of Classification Search ................. 250/282, 250/281, 288, 287
See application file for complete search history.

(56) References Cited

U.S. PATENT DOCUMENTS

| 7,429,729 | B2 * | 9/2008 | Schultz et al. | 250/287 |
|---|---|---|---|---|
| 7,538,321 | B2 * | 5/2009 | Ishimaru et al. | 250/288 |
| 2004/0245448 | A1 * | 12/2004 | Glish et al. | 250/281 |
| 2006/0057638 | A1 * | 3/2006 | Bosques et al. | 435/7.1 |
| 2006/0127950 | A1 * | 6/2006 | Bosques et al. | 435/7.1 |
| 2006/0148093 | A1 * | 7/2006 | Gygi et al. | 436/173 |
| 2006/0186331 | A1 * | 8/2006 | Hartmer et al. | 250/288 |
| 2006/0192100 | A1 * | 8/2006 | Zubarev et al. | 250/282 |
| 2006/0255263 | A1 * | 11/2006 | Ishimaru et al. | 250/288 |
| 2007/0057172 | A1 * | 3/2007 | Wang | 250/281 |
| 2007/0254371 | A1 * | 11/2007 | Kas et al. | 436/86 |
| 2009/0050798 | A1 * | 2/2009 | Jackson et al. | 250/282 |

FOREIGN PATENT DOCUMENTS

JP  2005-300420  4/2004

OTHER PUBLICATIONS

Zhang, J., et al., "Strategy for profiling and Structure Elucidation of Mucin-Type Oligosaccharides by Mass Spectrometry", Analytical Chemistry, vol. 76, No. 20, Oct. 15, 2004, pp. 5990-6001.

Hakansson, Kristina, et al., "Electron Capture Dissociation and Infrared Multiphoton Dissociation MS/MS of an N-Glycosylated Pryptic Peptide To Yield Complementary Sequence Information", Analytical Chemistry, vol. 73, No. 18, Sep. 15, 2001, pp. 4530-4536.

(Continued)

*Primary Examiner*—Jack I Berman
*Assistant Examiner*—Johnnie L Smith
(74) *Attorney, Agent, or Firm*—Stites & Harbison, PLLC; Juan Carlos A. Marquez, Esq.

(57) ABSTRACT

To analyze glycans and peptide sequences without liberating glycans from glycosylated peptides, a glycan structure is analyzed through negative-ion CID, in which sialic acid and fucose are resistant to elimination, and a peptide sequence is analyzed through positive-ion ECD.

11 Claims, 14 Drawing Sheets

OTHER PUBLICATIONS

Hogan, Jason M., "Complementary Structural Information from a Tryptic N-Linked Glycopeptide via Electron Transfer Ion/Ion Reactions and Collision-Induced Dissociation", Journal of Proteome Research, vol. 4, No. 2, 2005, pp. 628-632.

Deguchi, Kisaburo, et al., "Complementary structural information of positive- and negative-ion $MS^n$ spectra of glycopeptides with neutral and sialylated N-glycans", Rapid Communication Mass Spectrom, 2006, vol. 20, pp. 741-746.

* cited by examiner

Sialyl Lewis x Standard CID (MS$^2$)

Sialyl Lewis a Standard CID (MS$^2$)

CID (MS$^2$): 1139.1 [M-2H]$^{2-}$ →

CID (MS$^3$): 1418.6 [B$_5$-H]$^-$ →

PA 200.4 CID (MS$^2$): 858.4 [M−2H]$^{2-}$ →

PA 200.4 CID (MS$^3$): 1418.6 [B$_5$−H]$^-$ →

METHODS AND INSTRUMENTS FOR IDENTIFICATION OF GLYCOSYLATED PROTEINS AND PEPTIDES

CLAIM OF PRIORITY

The present application claims priority from Japanese application JP 2006-225715 filed on Aug. 22, 2006, the content of which is hereby incorporated by reference into this application.

FIELD OF THE INVENTION

The present invention relates to methods and instruments for analyzing biological materials using mass spectrometry. More specifically, it relates to methods and instruments for analyzing glycosylated proteins (glycoproteomics) and glycosylated peptides.

BACKGROUND OF THE INVENTION

Glycans on proteins are classified as N-glycans and O-glycans. In N-glycans, an amido group in a side chain of asparagine (N) is N-glycosylated. In O-glycans, an alcohol in a side chain of serine (S) or threonine (T) is glycosylated. Glycoproteomics places importance on determination of types of glycans (structures), and types and glycosylation sites of proteins. Glycosylated proteins can be converted into glycosylated peptides by enzymatic digestion such as tryptic digestion. Thus, they can be identified if the amino-acid sequences of glycosylated peptides can be analyzed and determined. In practice, however, glycans have complicated structures, and this inhibits satisfactory analysis of glycosylated peptides.

N-glycosylated peptides have been analyzed by a technique of liberating a glycosylation site from the peptide moiety through enzymatic digestion. It is difficult, however, to determine the types and glycosylation sites of the original peptides and proteins according to this technique, although constitutive glycans can be analyzed. As another possible solution, a technique has been proposed in which the glycosylation site of a peptide is labeled with an isotope upon separation of a glycan from the peptide through enzymatic digestion. It is difficult, however, to determine the types of glycans including structural isomers according to this technique, although the types and glycosylation sites of proteins can be determined. In analyses of O-glycosylated peptides, there has been proposed a technique of chemically derivatizing glycans. This technique, however, is independent of peptide analyses, and the acquired data are not satisfactorily tied with the peptide analyses (J. Zhang, L. L. Lindsay, J. L. Hedrick. C. B. Lebrilla, Strategy for profiling structure elucidation of mucin-type oligosaccharides by mass spectrometry, Analytical Chemistry Vol. 76 (2004) 5990-6001). Thus, different techniques have been applied to analyze N-glycans and to analyze O-glycans, respectively.

In contrast, attempts have been made to directly analyze glycosylated proteins and peptides by mass spectrometry without liberating glycans therefrom. JP-A No. 2005-300420, for example, discloses a technique for analyzing a glycosylated peptide by carrying out tandem mass spectrometry of protonated or cationized ions derived from the glycosylated peptide through collision-induced dissociation (CID) using a mass spectrometer. When an ion derived from the principal chain of a peptide and another ion derived from a glycan are separately and independently detected, these ions are further subjected to tandem mass spectrometry (MS/MS/MS), respectively, according to this technique. Thus, information on detected ions is simplified. In addition, there have been proposed a technique for analyzing a glycosylated peptide by subjecting a positive ion derived from the glycosylated protein to CID in combination with electron capture dissociation (ECD), infrared multi-photon dissociation (IRMPD), and/or electron transfer dissociation (ETD). This technique has been proposed by K. Hakansson, H. J. Cooper, M. R. Emmett, C. E. Costello, A. G. Marshall, C. L. Nilsson in Electron capture dissociation and infrared multiphoton dissociation MS/MS of an N-glycosylated tryptic peptide to yield complementary sequence information, Analytical Chemistry Vol. 73 (2001) 4530-4536, and by J. M. Hogan, S. J. Pitteri, P. A. Chrisman, C. A. McLuckey in Complementary structural information from a tryptic N-linked glycopeptide via electron transfer ion/ion reactions and collision-induced-dissociation, Journal of Proteome Research Vol. 4 (2005) 628-632. In addition, there has been proposed a technique for analyzing a glycosylated peptide by carrying out positive-ion CID tandem mass spectrometry in combination with negative-ion CID tandem mass spectrometry by K. Deguchi, H. Ito, Y. Takegawa, N. Shinji, H. Nakagawa, S. Nishimura in Complementary structural information of positive- and negative-ion MS" spectra of glycopeptides with neutral and sialylated N-glycans, Rapid Communications in Mass Spectrometry Vol. 20 (2006) 741-446.

SUMMARY OF THE INVENTION

It is difficult to determine the structure of an unknown glycan having a branched structure according to the technique described in JP-A No. 2005-300420. In the technique proposed by K. Hakansson et al. and by J. M. Hogan et al., ECD and ETD have substantially equivalent functions, and tandem mass spectrometry through ETD or ECD is advantageous to analyze peptides. It is, however, difficult to analyze glycans, because glycosylation sites are not dissociated. In contrast, according to tandem mass spectrometry through CID or IRMPD having equivalent functions, it is difficult to analyze glycan structures, because sialic acid and fucose in glycans are readily eliminated in positive ion analysis. According to the technique proposed by K. Deguchi et al., N-glycosylated samples can be analyzed, but O-glycosylated samples are difficult to be analyzed.

Analysis of glycosylated peptides places importance on determination of the types (structures) of glycans, and the types and glycosylation sites of proteins. Accordingly, it is desirable to carry out analyses of glycans and peptide sequences without liberating glycans from glycosylated peptides.

According to an aspect of the present invention, analyses of glycans and peptide sequences can be carried out without liberating glycans from glycosylated peptides, by analyzing glycan structures through negative-ion CID tandem mass spectrometry such as MS/MS or MS/MS/MS, and analyzing peptide sequences through positive-ion ECD tandem mass spectrometry such as MS/MS. Such negative-ion CID tandem mass spectrometry is not likely to cause elimination of sialic acid and fucose.

According to an aspect of the present invention, both O-glycosylated peptides and N-glycosylated peptides can be analyzed. Namely, the types (structures) of glycans, and the types and glycosylation sites of proteins can be determined according to the same analyzing procedure. In addition, the analysis can be carried out with less time and efforts, because the structures of glycosylated peptides are analyzed through mass spectrometry alone without liberating glycans from the glycosylated peptides.

DETAILED DESCRIPTION OF THE PREFERRED EMBODIMENTS

Some embodiments of the present invention will be illustrated below with reference to the attached drawings.

Figure 1:
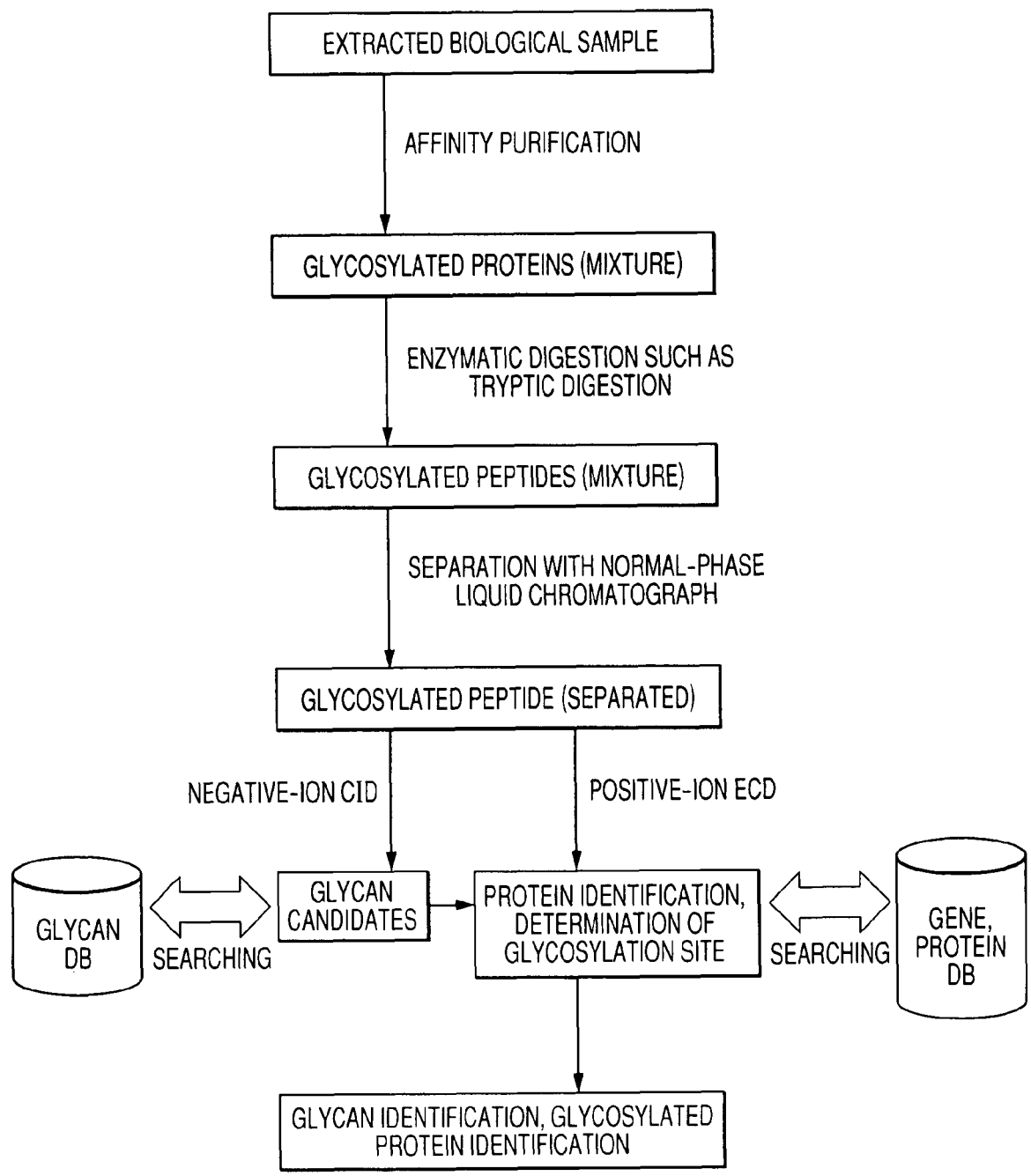
FIG. 1 is a diagram illustrating how glycosylated peptide structures are analyzed according to an embodiment of the present invention.

FIG. 1 illustrates how a sample is analyzed by a method for analyzing glycosylated peptide structures according to an embodiment of the present invention. To analyze a glycosylated protein (mixture) extracted from a biological material, such as blood, the extracted biological sample is subjected to affinity purification typically with lectin and further subjected to enzymatic digestion such as tryptic digestion to yield a glycosylated peptide (mixture).

The glycosylated peptide (mixture) is separated typically with a normal-phase liquid chromatograph. When a liquid chromatograph/mass spectrometer (LC/MS) system is used, separated components are sequentially introduced into an ion source of the mass spectrometer.

In ionic analysis with a mass spectrometer, negative ions derived from a glycosylated peptide are initially analyzed, and positive ions derived therefrom are then analyzed. By using a mass spectrometer that can switch between positive- and negative-ion analysis modes at high speed, data acquisition is completed in one analysis. If not, two analyses including a negative-ion analysis and a positive-ion analysis should be carried out.

In the negative-ion analysis, negative ions derived from a glycosylated peptide are subjected to MS/MS through collision-induced dissociation (CID). When there are precursor ion candidates having such ion intensities as to yield data having sufficient fragment ion information even after MS/MS, it is desirable to select an ion having a valency as high as possible as a precursor ion. This is because the selected precursor ion is expected to yield abundant fragment ion information in the resulting MS/MS analysis data (spectrum). To determine whether or not a glycosylated peptide is detected, the masses of fragment ions detected in MS/MS analysis data are calculated, and whether or not an ion having the greatest mass among glycan ions containing monosaccharide glycosidic linkages alone is detected. The calculation process herein will be mentioned below. When the detection of a glycosylated peptide is verified, MS/MS/MS analysis is carried out using the ion having the greatest mass among glycan ions containing monosaccharide glycosidic linkages alone as a precursor ion. These calculations should be carried out in real time upon analysis.

After the completion of data acquisition in negative-ion analysis, the component which has been identified to be a glycosylated peptide is fed to an ion source to form positive ions. MS/MS through electron capture dissociation (ECD) or electron transfer dissociation (ETD) is then carried out using these positive ions as precursor ions. It should be noted that such positive ions derived from a glycan peptide include not only protonated molecules such as $[M+H]^+$ and $[M+2H]^{2+}$, but also cationized ions such as $[M+Na]^+$, $[M+2Na]^{2+}$, and $[M+Na+H]^{2+}$.

The above illustration has been made by taking an on-line analysis using LC/MS. Data can also be acquired by an off-line analysis using fraction samples of components separated by LC. In this case, calculations relating to the selection of a precursor ion in negative-ion MS/MS/MS analysis are not necessarily conducted in real time upon analysis.

In this connection, a glycan database has been prepared by subjecting various glycan standards to negative-ion MS/MS and/or MS/MS/MS to yield data. This database contains the data in combination with the masses (m) and charge numbers (z), or m/z, of corresponding precursor ions.

The database containing analysis data of standards is then searched against negative-ion MS/MS/MS analysis data acquired in actual analysis to thereby determine glycan candidates including their structures typically through profile matching of the analysis data. A key in this technique is to check between the data of standards and the actual data. The data of standards therefore do not always have to be a database when the checking can be carried out manually.

In contrast, on the positive ion analysis data, a gene or protein database is searched as with regular proteomic analysis. In this procedure, it is important to reflect the mass information of glycan candidates to the database searching. This contributes to identification of proteins, determination of glycosylation sites, and determination of glycans.

This technique is very effective even in analysis of unknown samples, because both O-glycosylated proteins and N-glycosylated proteins can be analyzed according to the same procedure.

Figure 2:
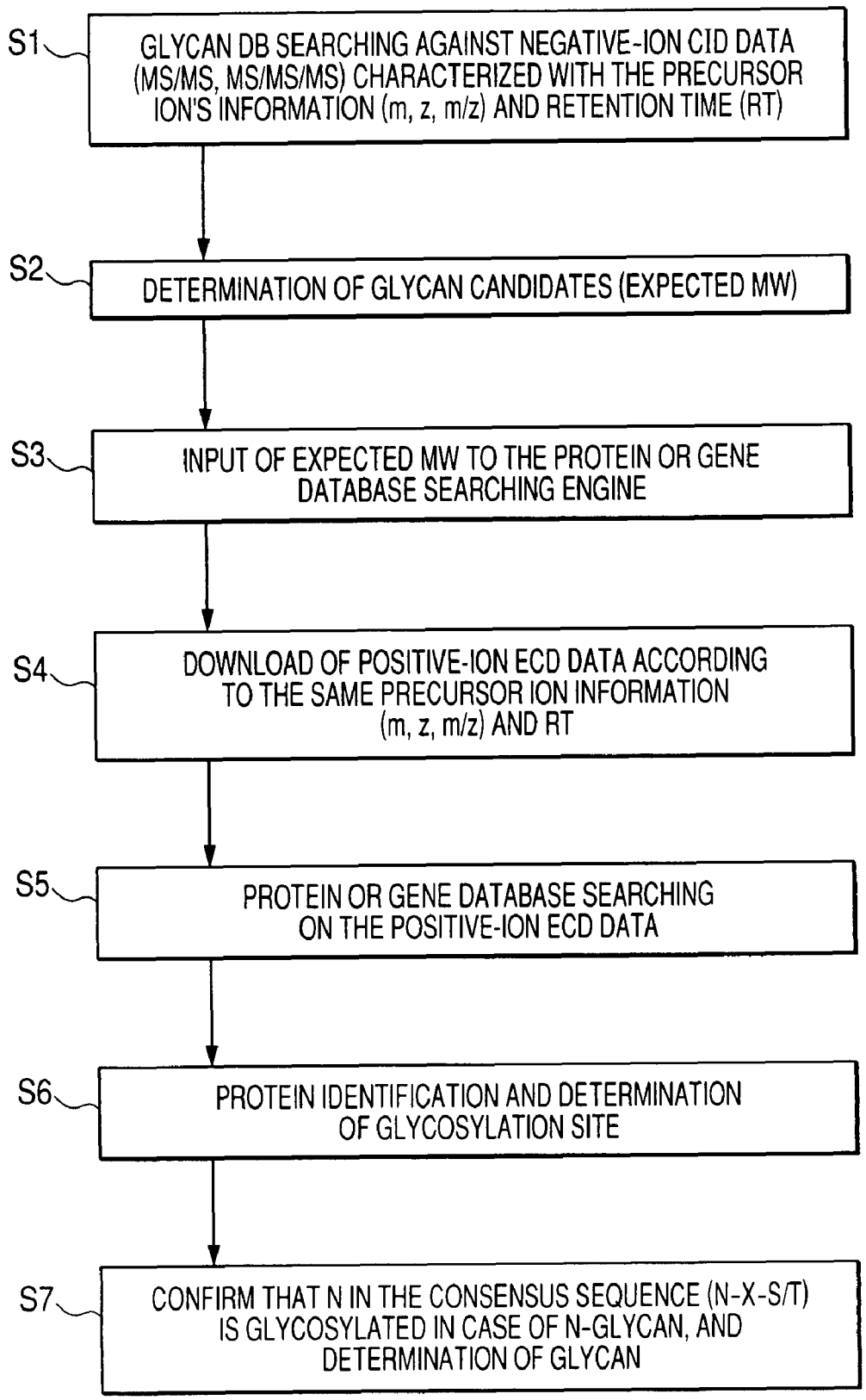
FIG. 2 is a detailed illustration of how measured data are analyzed.

FIG. 2 illustrates how measured data are analyzed. Initially, a glycan database is searched against negative-ion MS/MS or MS/MS/MS analysis data (Step 1). Glycan candidates for identification are determined (Step 2). In this step, a target glycan can only be roughly identified. Specifically, when the target glycan is a N-glycan, GlcNAc (N-acetylglucosamine) sites and GlcNAc-Fuc (fucose) sites may be eliminated in CID process. In contrast, O-glycans are resistant to such elimination. The molecular weight information of the determined glycan candidates is reflected to conditions for the subsequent gene or protein database searching (Step 3). Specifically, asparagine alone is a candidate of amino acid at the glycosylation site for N-glycans, and serine and threonine are candidates of amino acids at the glycosylation site for O-glycans. The molecular weight information of these amino acids are combined with mass information when these amino acids are glycosylated, positive ion ECD data is downloaded (Step 4), and a protein or gene database is searched (Step 5). A searching software such as Mascot (supplied from Matrix Science Ltd.) can be used in the database searching. In addition, a de novo analysis software for amino acid sequencing can also be used.

When a gene database, for example, is searched, the gene database contains only base sequence information of genes and corresponding protein information. According to a database searching software, these data are converted into amino-acid sequence data using the fact that one amino acid is encoded by three bases. When a protein is converted into peptides by enzymatic digestion such as tryptic digestion as in the procedure in FIG. 1, the resulting peptides have a specific amino acid such as lysine or arginine at C-terminus. Amino-acid sequences of all theoretically possible peptides are calculated. Assuming that these peptides give protonated ions, and that their fragment ions are dissociated at peptide linkage sites, m/z values of fragment ions can be calculated using molecular weights of amino acids to thereby constitute virtual MS/MS analysis data. Upon calculation, glycosylated amino acids are to be calculated as having increased masses by the masses of modifying glycans. Thus, MS/MS analysis data on all possible cases can be calculated. By checking the vertical MS/MS analysis data with actual MS/MS analysis data according typically to correlation, the original protein or peptide can be identified, and the amino acid at the glycosylation site can be determined. When a protein database is used, an analysis can be carried out in the same manner, except that the protein database contains protein's amino-acid sequence information.

Data for use in actual database searching must be data of peptide glycosylated with the same glycan with the negative-ion analysis. This should be verified by checking LC retention time information and/or precursor ion information in Step 4. By carrying out database searching on ECD or ETD analysis data, the protein is identified and the glycosylation site is determined (Step 6). When asparagine is a glycosylated amino acid, a consensus sequence (N-X-S/T) should be verified, wherein N represents asparagine, X represents an amino acid other than proline, and S/T represents serine or threonine. The consensus sequence is specific to the vicinity of N-glycosylation site. Finally, the glycan can be selected from among glycan candidates based on the molecular weight of the glycosylation site (Step 7).

Figure 3:
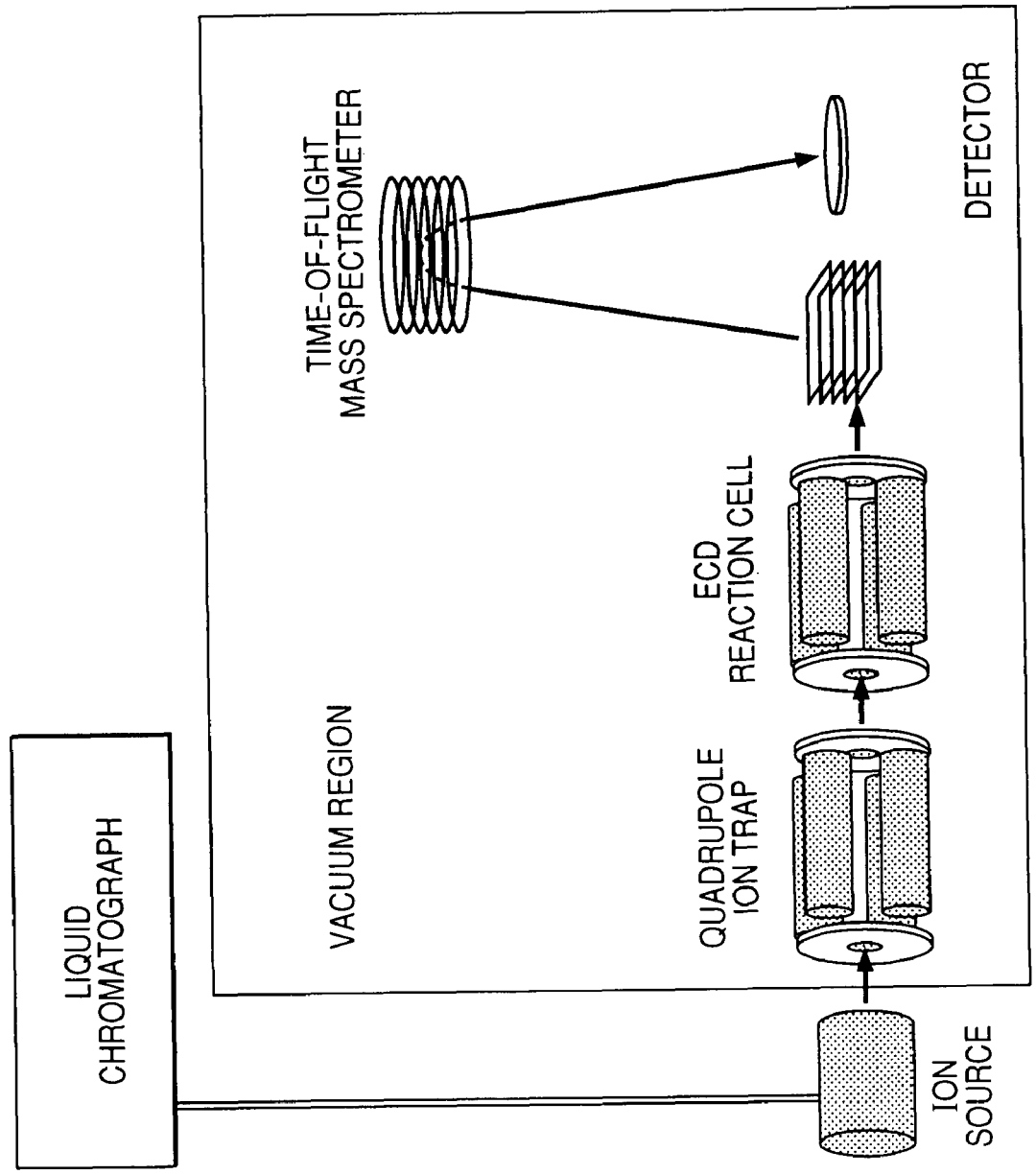
FIG. 3 is a schematic view of a typical liquid chromatograph/mass spectrometer (LC/MS) for use in a method for analyzing glycosylated peptide structures according to an embodiment of the present invention.

FIG. 3 is a schematic view of a typical LC/MS used in a method for analyzing glycosylated peptide structures according to an embodiment of the present invention. Requirements for a mass spectrometer will be illustrated. The mass spectrometer is required to carry out positive- and negative-ion analysis. In negative-ion analysis mode, it is required to carry out CID MS/MS analysis and is desirably capable of carrying out MS$^n$ analysis such as MS/MS/MS analysis. In positive-ion analysis mode, it is required to carry out MS/MS analysis through ECD or ETD. It is desirably capable of periodically switching between positive- and negative-ion analysis modes within about one second.

The mass spectrometer illustrated in FIG. 3 has a vacuum region. In the vacuum region, the masses of ions are highly precisely determined with a time-of-flight mass spectrometer; negative-ion CID MS/MS analysis or MS/MS/MS analysis is carried out with a quadrupole (radio frequency) ion trap; and positive-ion ECD MS/MS analysis is carried out with an ECD cell. The ECD cell is often actually composed of a quadrupole (radio frequency) ion trap, because it requires some reaction time. Accordingly, CID and ECD can be carried out with one cell. This is also true for ETD. When positive- and negative-ion analysis modes are switched at high speed, the selection of precursor ions in negative-ion MS/MS/MS analysis is especially important. It is desirable that the mass spectrometer can carry out MS/MS/MS analysis using all fragment ions detected in MS/MS analysis data as precursor ions at very high speed. If not, the mass spectrometer should be capable of selecting, as a precursor ion, an ion having the greatest mass among glycan ions containing monosaccharide glycosidic linkages alone in real time upon analysis. To calculate m/z of a glycan ion containing monosaccharide glycosidic linkages alone, molecular weights M are determined based on the molecular weights of monosaccharides mentioned below, while considering that the molecular weight (Da) is decreased by 18 per one glycosidic linkage. In the case of N-glycans, the molecular weight is further decreased by 18. Next, m/z of a singly-charged ion is determined to be M−1, and m/z of a doubly-charged ion is determined to be (M−2)/2, because negative ions derived from glycosylated peptides and glycans are deprotonated molecules such as $[M-H]^-$ and $[M-2H]^{2-}$. The charge numbers of ions are determined by determining difference in m/z between monoisotopic peak and isotopic peak in mass spectrometric data.

| | |
|---|---|
| Hexoses (galactose, mannose, and glucose) | 180.05 |
| HexNAc (N-acetylglucosamine and N-acetylgalactosamine) | 221.08 |
| Deoxyhexoses (fucose and rhamnose) | 164.06 |
| Pentose (xylose) | 150.04 |
| NeuAc (N-acetylneuraminic acid) | 309.10 |
| NeuGc (N-glycolylneuraminic acid) | 325.09 |

When on-line analysis with switching between positive- and negative-ion analysis modes is not carried out, a sample may be analyzed, for example, by separating components typically through normal-phase liquid chromatography, fractionating the separated components, introducing the fractionated components into the ion source using a syringe pump, and sequentially carrying out negative-ion analysis and positive-ion analysis. A method for analysis according to an embodiment of the present invention will be illustrated by taking specific data as an example.

[Illustrative Analysis of O-Glycosylated Peptide]

Figure 4A:
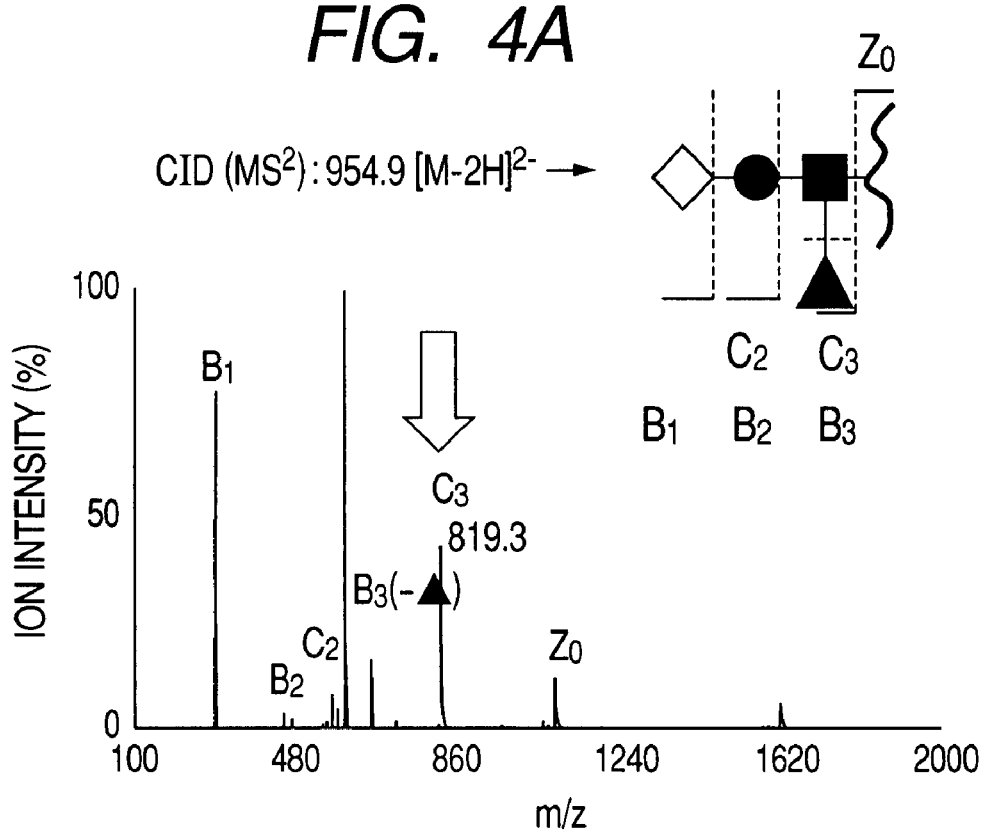
FIGS. 4A and 4B are diagrams illustrating CID MS/MS analysis data and CID MS/MS/MS analysis data, respectively, of negative ions (deprotonated molecules) derived from a glycosylated peptide.
Figure 4B:
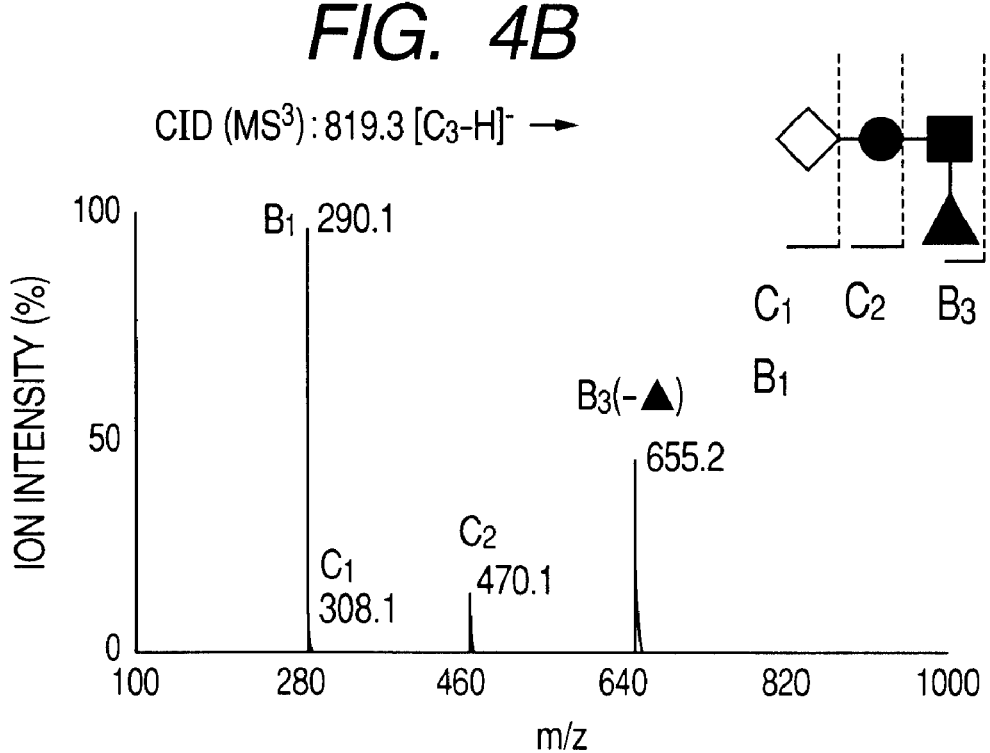

FIGS. 4A and 4B illustrate CID analysis data of negative ions (deprotonated molecules) derived from a glycosylated peptide. The precursor ion herein is $[M-2H]^{2-}$ with m/z of 954.9, in which M represents a glycosylated peptide molecule, and H represents a hydrogen atom. The precursor ion is a doubly-charged ion from which two protons have been removed. FIG. 4A shows CID MS/MS analysis data of the precursor ion. The upper right view in FIG. 4A is a schematic view of a glycosylation site, in which "B" and "C" represent ions dissociated at glycosidic linkage sites; the wavy line represents a peptide; the open diamond represents Neu5Ac (N-acetylneuraminic acid); the closed circle represents Gal (galactose); the closed square represents GlcNAc (N-acetylglucosamine); the closed triangle represents Fuc (fucose); and the broken lines represent dissociation sites.

With reference to FIG. 4A, an ion is identified to be a deprotonated molecule [M–H]⁻ of a glycan when m/z of the ion peak agrees with a value acquired by subtracting the product of the number of glycosidic linkages and 18 from the sum of molecular weights of the monosaccharides, and further subtracting 1 therefrom. The subtraction of 1 corresponds to deprotonation. By applying this calculation process, many ions dissociated at glycosidic linkage sites are detected, and an ion having the greatest mass among ions of glycans having monosaccharide glycosidic linkages is found to be the ion $C_3$ with m/z of 819.3 (=309.1+180.05+221.08+164.06-18×3-1). Since the glycan detection is verified, the ion $C_3$ is selected as a precursor ion. FIG. 4B shows CID MS/MS/MS analysis data acquired using this precursor ion. Since the sum of masses of $C_3$ and $Z_0$ corresponds to the mass of the precursor ion, the modifying glycan is expected to be an O-glycan, and the ion $Z_0$ is determined to be an ion of unmodified (unglycosylated) peptide.

Figure 5A:
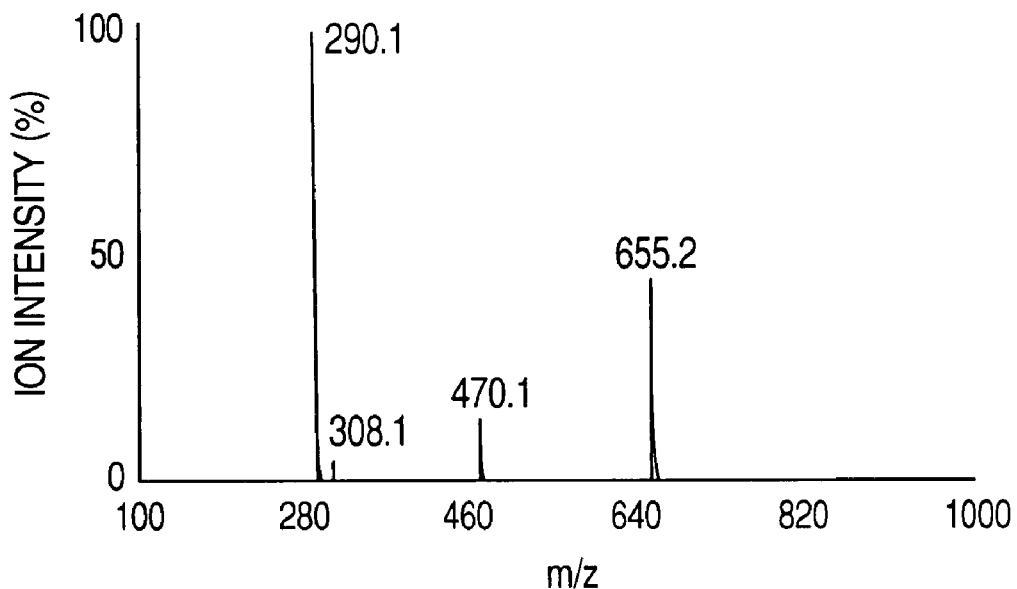
FIGS. 5A and 5B are diagrams illustrating data relating to sialyl Lewis x and sialyl Lewis a, respectively, hit in a glycan database searching.
Figure 5B:
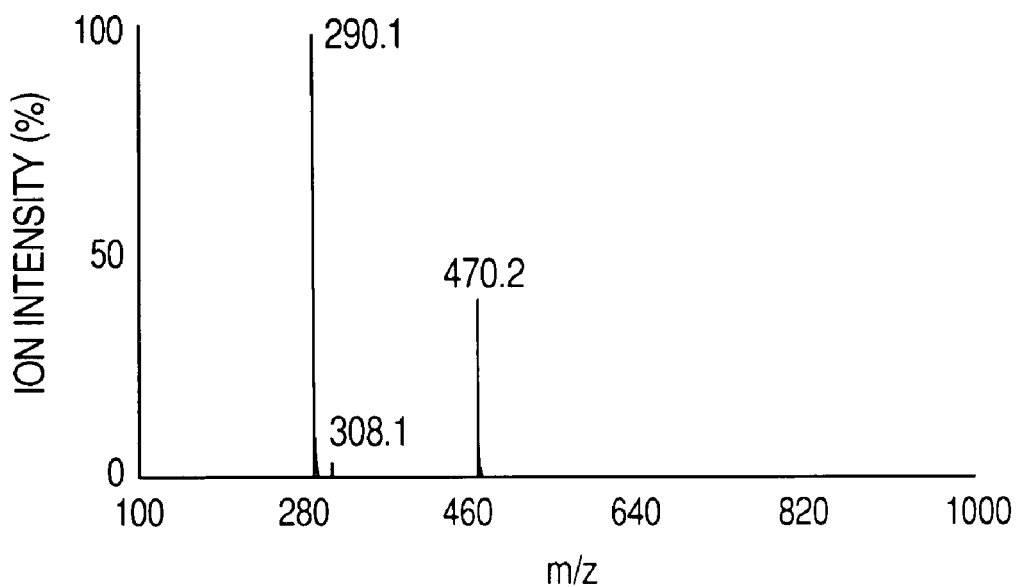

The glycan database contains the m/z values of fragment ions, relative intensities of their ion peaks, and CID voltage (gain) dependencies of the relative intensities. The glycan database may further contain MS/MS spectra determined at different CID voltages (gains). FIGS. 5A and 5B show the data, except for the CID voltage (gain) dependencies, hit in the glycan database searching. The data in FIGS. 5A and 5B are negative-ion MS/MS analysis data of standards of Sialyl Lewis x and Sialyl Lewis a, respectively. A fragment ion with m/z of 655.2 is detected in the data relating to Sialyl Lewis x but is not detected in the data relating to Sialyl Lewis a. The data relating to Sialyl Lewis x shows higher similarity with the data in FIG. 4B than the data relating to Sialyl Lewis a does, indicating that the tested sample has a glycan structure including Sialyl Lewis x modified with Fuc (fucose). In this connection, the glycan structure can be determined using a glycan database based on the MS/MS analysis data in FIG. 4A alone, but it requires complicated analyzing procedures.

Figure 6:
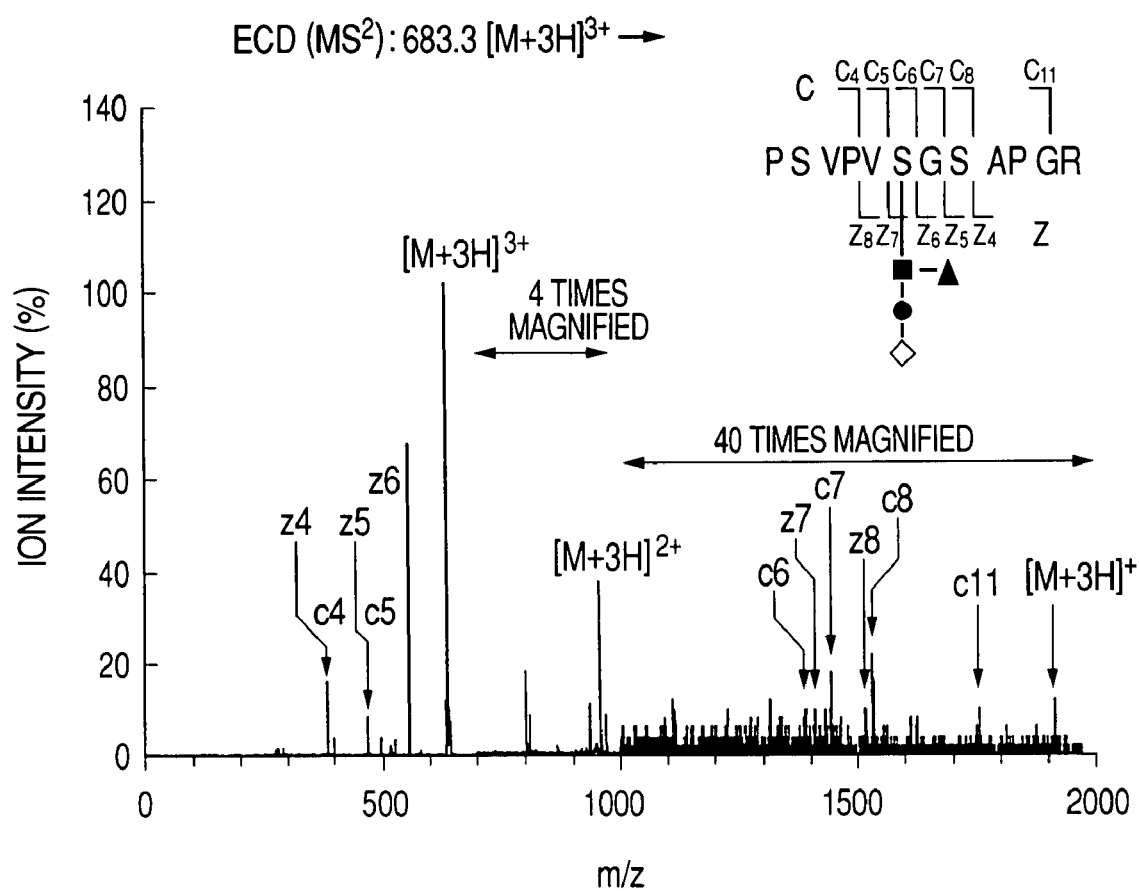
FIG. 6 is a diagram illustrating ECD MS/MS analysis data.

FIG. 6 shows positive-ion ECD MS/MS analysis data corresponding to the negative-ion analysis data in FIGS. 4A and 4B. According to ECD, peptide linkages are dissociated at specific sites to yield c ions and z ions. The upper right view in FIG. 6 shows the structure of a glycosylated peptide and detected ions derived therefrom. The alphabetical letters arranged horizontally represent an amino-acid sequence. A database searching was conducted on the MS/MS analysis data, many c ions and z ions giving amino-acid sequence information were detected, to thereby identify the original protein. The database searching also reveals that the seventh amino-acid serine (S) from the C-terminus is glycosylated with a glycan, demonstrating that the modifying glycan is an O-glycan. The precursor ion employed in the data is $[M+3H]^{3+}$ with m/z of 638.3. It is also desirable in ECD analysis to select, as a precursor ion, an ion having a precursor ion intensity at a specific level or more and a high charge number, from the viewpoint of fragment ion information. The ECD MS/MS analysis also detects ions corresponding to the precursor ion, except for having reduced charge numbers as a result of electron capture recombination ($[M+3H]^{2+}$ and $[M+3H]^{+}$).

[Illustrative Analysis of N-Glycosylated Peptide]

Analysis of another typical glycosylated peptide will be illustrated with reference to FIGS. 7A, 7B, 8A, 8B, and 9.

Figure 7A:
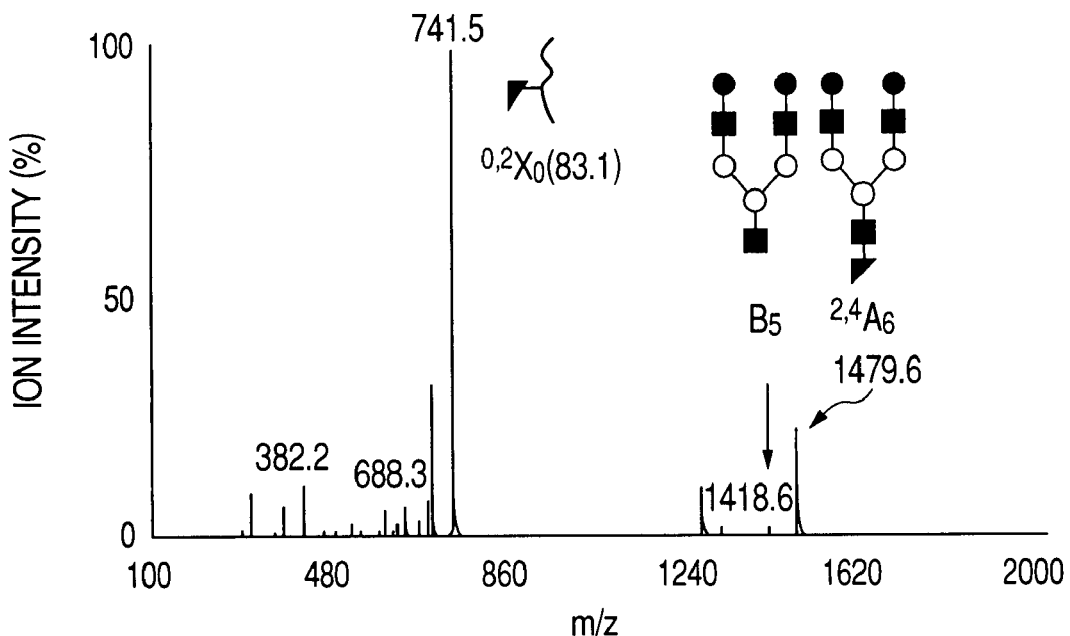
FIGS. 7A and 7B are diagrams illustrating CID MS/MS analysis data and CID MS/MS/MS analysis data, respectively, of negative ions derived from another glycosylated peptide.
Figure 7B:
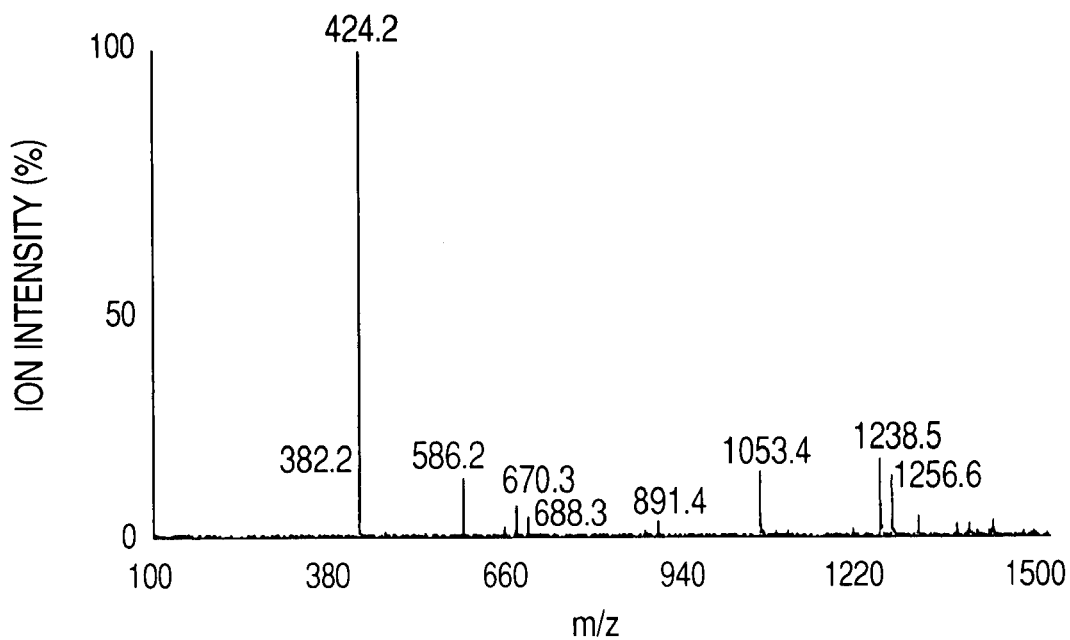

FIGS. 7A and 7B are diagrams illustrating CID analysis data of negative ions derived from a glycosylated peptide. The precursor ion used in the analysis is $[M-2H]^{2-}$ with m/z of 1139.1. FIG. 7A shows CID MS/MS analysis data of the precursor ion. The upper right view in FIG. 7A is a schematic view of a glycosylation site, in which the closed circle represents Gal (galactose), the closed square represents GlcNAc (N-acetylglucosamine), and the open circle represents Man (mannose). An ion having the greatest mass among ions of glycans having monosaccharide glycosidic linkages is found to be the ion $B_5$ with m/z of 1418.6 (nearly equals 180.05× 2+221.08×3+180.05×3-18×8-1). In this calculation, the number as acquired by multiplying 18 by (the number of glycosidic linkages plus 1) is subtracted, because the glycan is an N-glycan. This illustrated glycan gives relatively small numbers of different ions as detected. Since the glycan detection is verified, the ion with m/z of 1418.6 is selected as a precursor ion. FIG. 7B shows CID MS/MS/MS analysis data acquired using this precursor ion. The ion $A_6$ is not selected as the precursor ion, because it is an ion including $B_5$ combined with dissociated GlcNAc.

Figure 8A:
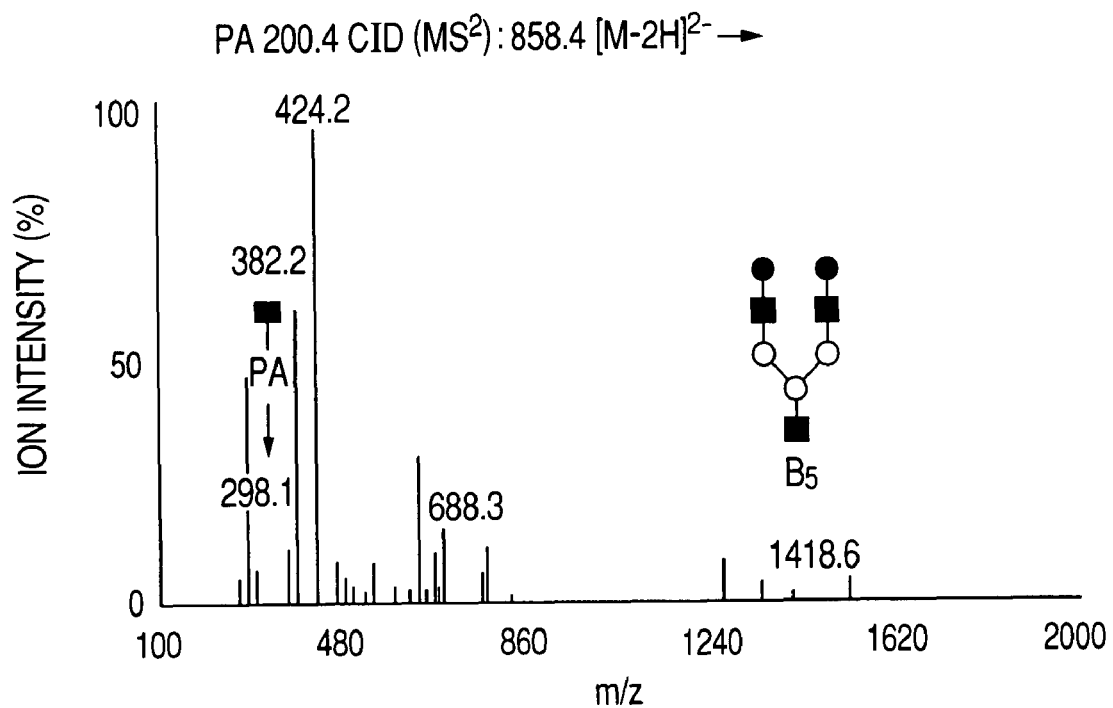
FIGS. 8A and 8B are diagrams illustrating MS/MS data and MS/MS/MS data retrieved from a glycan database against the data in FIGS. 7A and 7B.
Figure 8B:
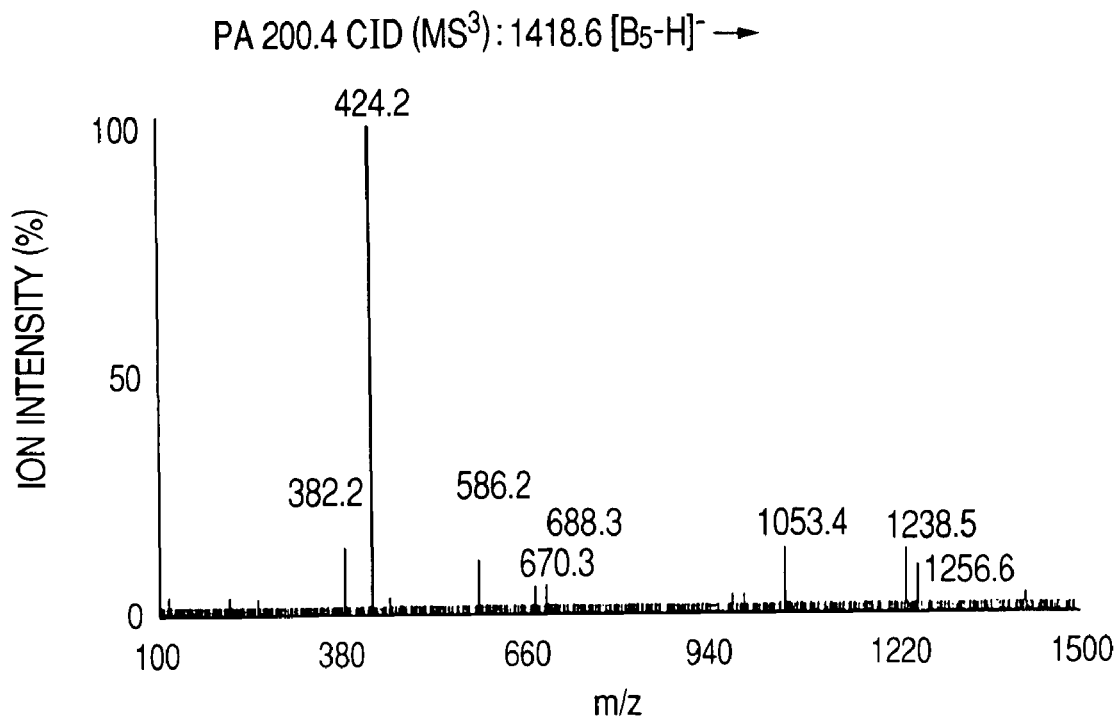
Figure 9:
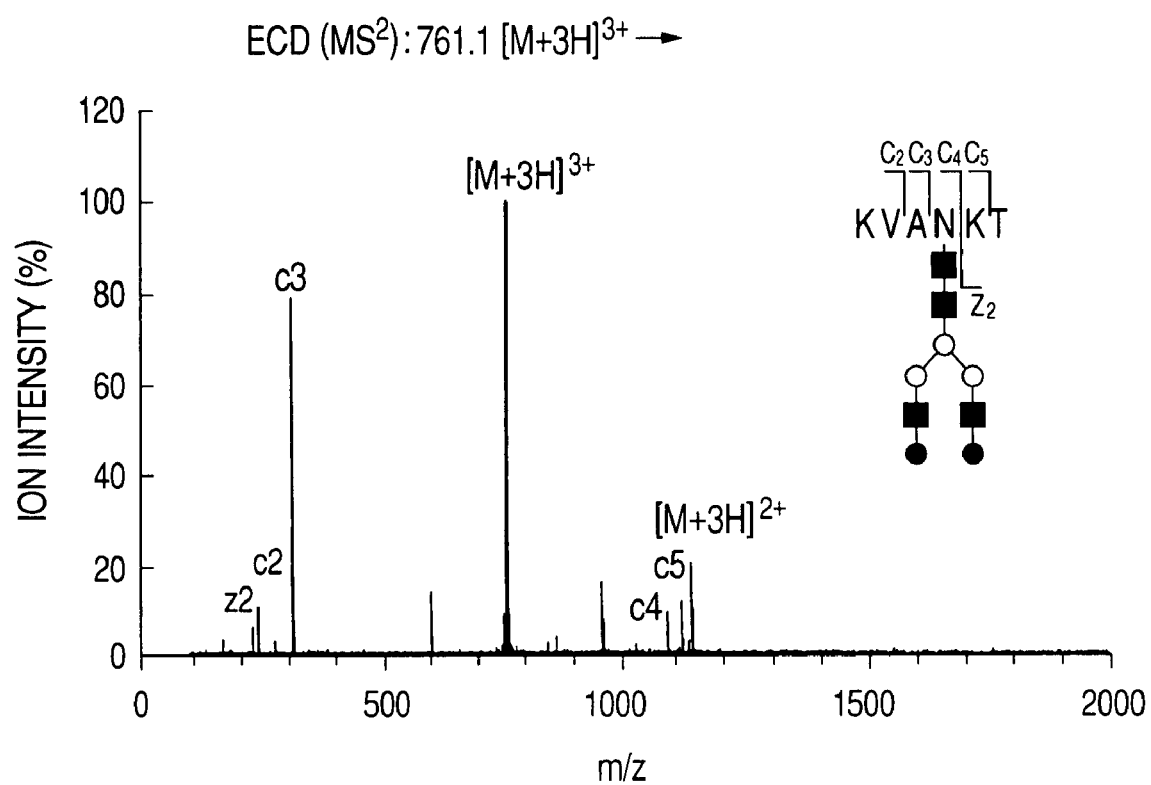
FIG. 9 is a diagram illustrating ECD MS/MS analysis data.

FIG. 8B shows the result of glycan database searching on the data in FIG. 7B. The data are data searched against a glycan called "200.4" which has been pyridylaminated (PA). Authentic samples of N-glycans have been generally subjected to derivatization such as pyridylamination. The data in FIG. 8B are therefore explained as MS/MS/MS analysis data of "200.4" glycan having a structure shown in the upper right view of FIG. 8A. In addition, the presence of the ion $A_6$ (FIG. 7A) indicates that the original modifying glycan is probably "200.4" glycan combined with a peptide with the interposition of GlcNAc. The original protein is identified and the glycosylation site is determined by carrying out a gene database searching on ECD MS/MS analysis data in FIG. 9 using the molecular weight of the modifying glycan. In addition, the molecular weight of the modifying glycan also reveals that the original glycan is the "200.4" glycan combined with a peptide with the interposition of GlcNAc. The consensus sequence (N-X-S/T) in this example is found to be N-K-T, which agrees with the fact that this glycan is an N-glycan. As has been described above, a method for analyzing glycosylated peptides according to an embodiment of the present invention can analyze both O-glycosylated peptides and N-glycosylated peptides according to the same analysis procedure.

Figure 10:
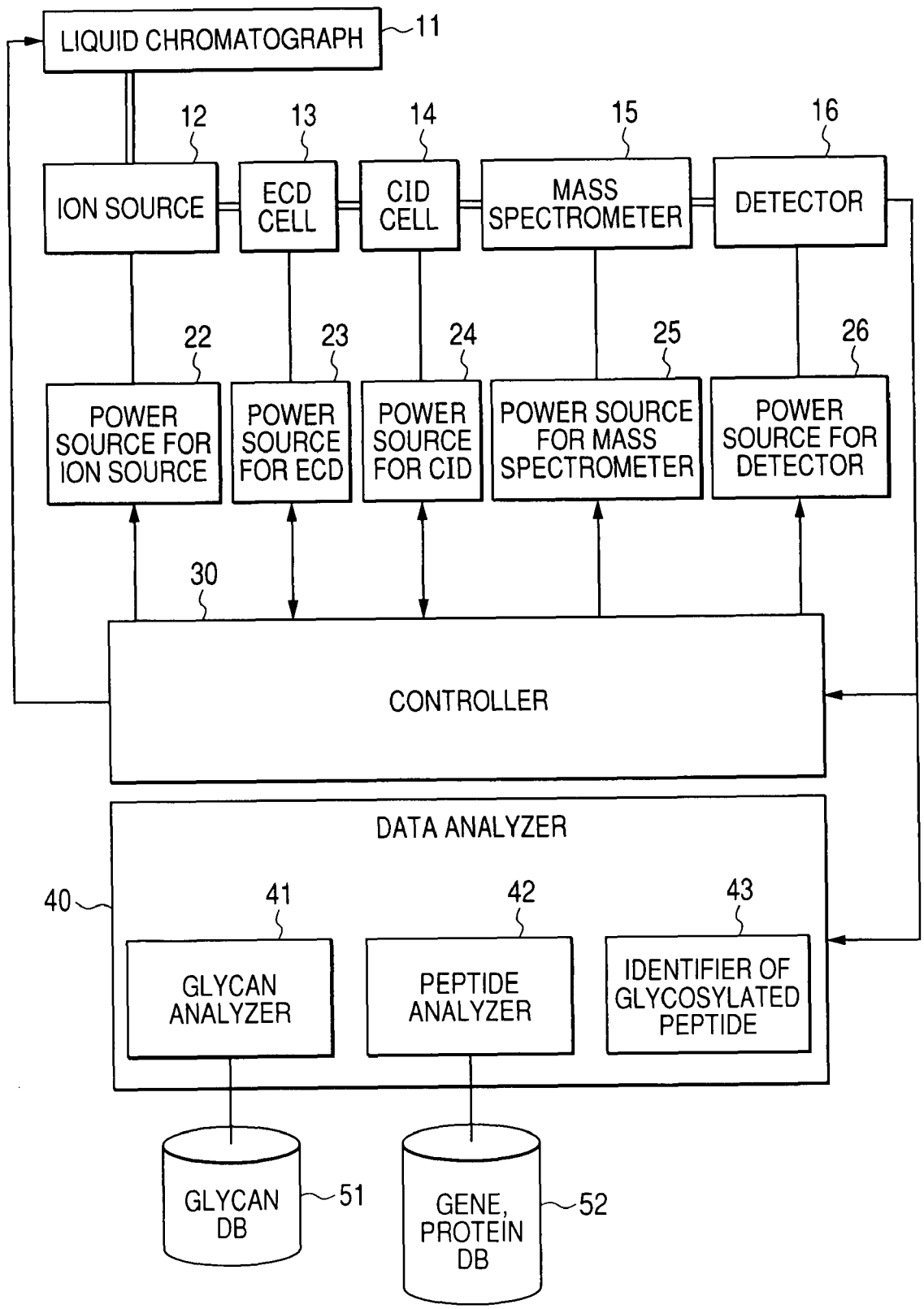
FIG. 10 is a block diagram illustrating an LC/MS for use in a method for analyzing glycosylated peptide structures according to an embodiment of the present invention.

FIG. 10 is a block diagram illustrating an LC/MS for use in a method for analyzing glycosylated peptide structures according to an embodiment of the present invention. The instrument according to this embodiment includes a liquid chromatograph 11, an ion source 12, an ECD cell 13, a CID cell 14, a mass spectrometer 15, a detector 16, power sources 22 to 26, a controller 30, and a data analyzer 40. A sample separated through the liquid chromatograph 11 is introduced into the ion source 12 to form ions. The ions are introduced into the ECD cell 13 and the CID cell 14. The detector 16 detects ions after mass spectrometry. The power sources 22 to 26 drive these components. The controller 30 controls the power sources 22 to 26 and the liquid chromatograph 11 with reference to the detection signals from the detector 16. The data analyzer 40 includes a glycan analyzer 41, a peptide analyzer 42, and an identifier of glycosylated peptide 43. The glycan analyzer 41 selects glycan candidates by checking mass spectrometric data from the detector 16 with data in a glycan database 51. The peptide analyzer 42, for example, base sequence information stored in a gene/protein database 52 into amino-acid sequence data, calculates amino-acid sequences of peptides from the amino-acid sequence data to constitute a virtual mass spectrometric data in consideration of glycan candidates, and checks the virtual mass spectrometric data with the actual mass spectrometric data from the detector 16. The identifier of glycosylated peptide 43 corrects processes of the peptide analyzer 42 based on the information on glycan candidates from the glycan analyzer 41 and determines the glycosylation site.

Glycosylated peptides separated in the liquid chromatograph 11 are sequentially fed to the ion source 12 and are converted into negative or positive ions. Positive- and negative-ion analysis modes are switched by transmitting signals from the controller 30 to the power sources 22 to 26 for the ion source 12, the ECD cell 13, the CID cell 14, the mass spectrometer 15, and the detector 16. Initially, negative-ion analysis is conducted in the following manner. Negative ions converted in the ion source 12 pass straight through the ECD cell 13 and CID cell 14, and are subjected to mass spectrometry in the mass spectrometer 15. A selected precursor ion is subjected to CID in the CID cell 14, and formed ions (fragment ions) are subjected to mass spectrometry in the mass spectrometer 15. Thus, MS/MS analysis data are acquired. If one or more ions derived from a glycan having monosaccharide glycosidic linkages are detected, an ion having a greatest mass among them is selected as a precursor ion, and the precursor ion is subjected typically to MS/MS/MS analysis. Next, the analysis mode of the mass spectrometer 15 is switched to the positive-ion analysis mode, and positive ion analysis is conducted in the following manner. Positive ions converted in the ion source are subjected to mass spectrometry to yield mass spectrometric data. The same component as with the negative-ion analysis is selected as a precursor ion, and the precursor ion is subjected to ECD in the ECD cell 13. The ions (fragment ions) formed in ECD are subjected to mass spectrometry in the mass spectrometer 15 to thereby carry out MS/MS analysis. If no ion derived from a glycan is detected in the negative-ion CID MS/MS analysis data, there is no need of switching the analysis mode to the positive-ion analysis mode. If different precursor ions are detected, negative-ion CID MS/MS analysis data acquisition is carried out on each of them, respectively.

Figure 11:
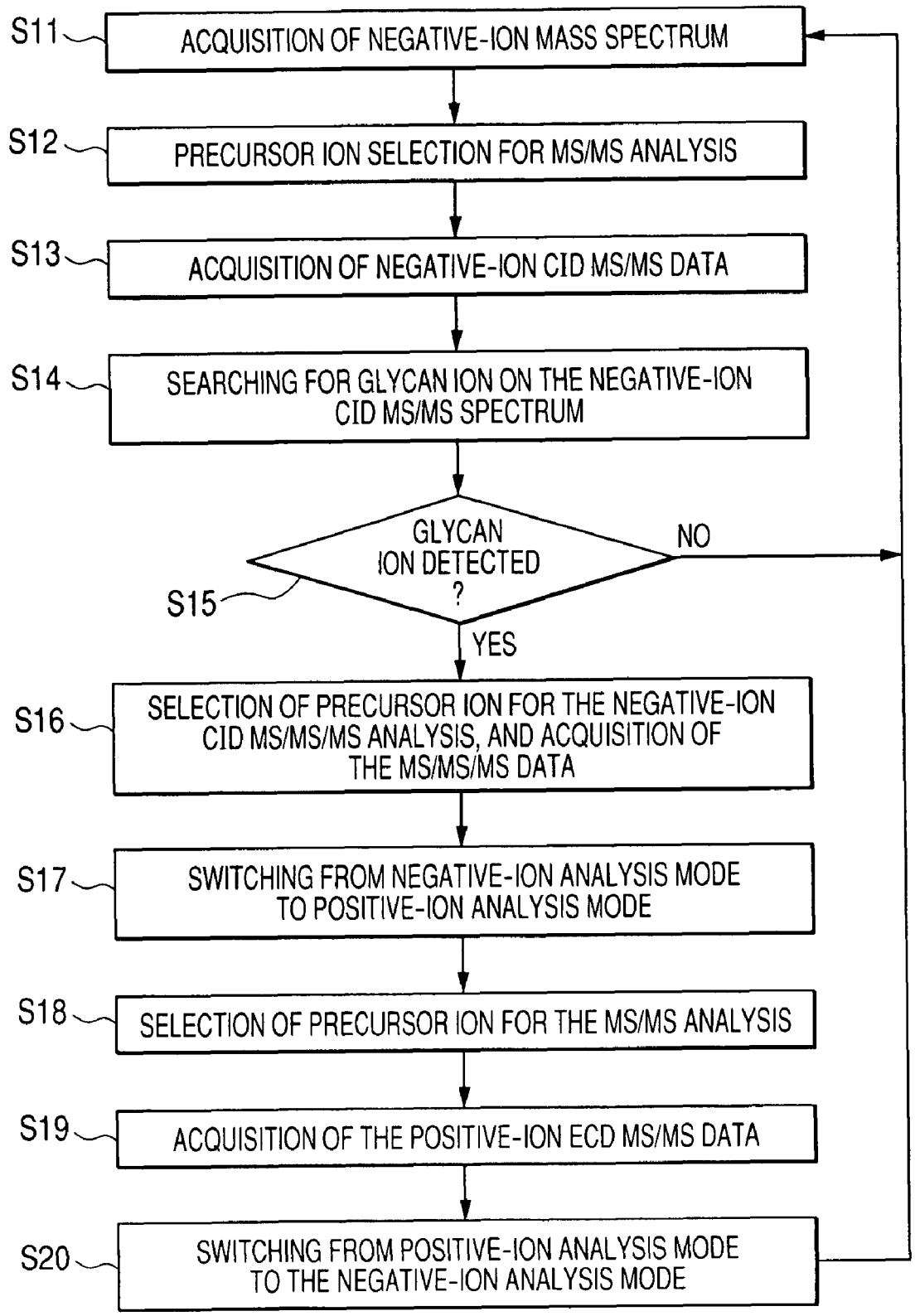
FIG. 11 is a flow chart of MS analysis typically in an LC/MS for use in a method for analyzing glycosylated peptide structures according to an embodiment of the present invention.

FIG. 11 is a flow chart of MS analysis typically in an LC/MS for use in a method for analyzing glycosylated peptide structures according to an embodiment of the present invention. Initially, negative ions are formed, and negative-ion mass spectrometric data (mass spectrum) are acquired (Step 11). Next, a precursor ion for MS/MS analysis is selected from among the detected ions, according to the ion intensity, the charge number, and the range of m/z (Step 12). The CID MS/MS analysis data of the selected precursor ion are acquired (Step 13). Whether or not a glycan ion is detected in MS/MS analysis data is determined in real time (Step 14). Specifically, whether or not a singly-charged ion is detected is determined, which singly-charged ion has such m/z as acquired by subtracting the product of the number of glycosidic linkages and 18 from the sum of molecular weights of the monosaccharides, and further subtracting 1 therefrom. If no ion having m/z agreeing with the calculated value is detected (Step 15, NO), the procedure is returned to the negative-ion mass spectrometric data acquisition in S11. If one or more ions having m/z agreeing with the calculation result are detected (Step 15, YES), an ion having the greatest mass is selected as a precursor ion, and negative-ion CID MS/MS analysis data on the precursor ion are acquired (Step 16).

The analysis mode of the mass spectrometer is then switched from the negative-ion analysis mode to the positive-ion analysis mode, and positive-ion mass spectrometric data (mass spectra) are acquired (Step 17). A precursor ion for positive-ion ECD MS/MS analysis, corresponding to the precursor ion in the negative-ion MS/MS analysis is selected from among detected ions (Step 18). The precursor ion for negative-ion analysis is a deprotonated molecule represented by $[M-nH]^{n-}$ in which "n" represents a natural number, whereas the corresponding precursor ion for positive-ion analysis is a protonated molecule represented by $[M+mH]^{m+}$ in which "m" represents a natural number, or a cationized molecule represented typically by $[M+Na]^+$, $[M+2Na]^{2+}$, or $[M+Na+H]^{2+}$. When the precursor ion for negative-ion analysis is, for example, a doubly-charged ion, the mass m of the precursor ion is $2(m/z)+2$. When the precursor ion for positive-ion analysis is a triply-charged protonated molecule, the m/z of the precursor ion is $(m+3)/3$. The charge number of an ion is determined by determining the difference in m/z between a monoisotopic ion and an isotopic ion in ion peak. Specifically, if the ion is a doubly-charged ion, the difference in m/z is 0.5. If it is a triply-charged ion, the difference in m/z is 0.33. After positive-ion ECD MS/MS analysis data are acquired (Step 19), the analysis mode of the mass spectrometer is switched from the positive-ion analysis mode to the negative-ion analysis mode (Step 20). According to this analysis flow, the analysis mode is not switched to the positive-ion analysis mode unless one or more ions derived from glycans are detected in the negative-ion analysis. Accordingly, analysis data of glycan ions detected in negative-ion analysis mode can be efficiently acquired.

The analysis can be conducted with higher throughput by simultaneously carrying out negative-ion CID in the CID cell and positive-ion ECD in the ECD cell, because a dissociation reaction time in the ECD cell may be longer than a dissociation reaction time in the CID cell. In this case, analysis is conducted in the following manner. Initially, negative ions are formed in the ion source and are subjected to negative-ion MS/MS analysis in the CID cell to acquire analysis data. Next, if a glycan-derived ion is detected, positive ions are formed in the ion source and are subjected to mass spectrometry to acquire mass spectrometric data. Thus, a precursor ion is determined, and the precursor ion is subjected to positive-ion dissociation reaction in the ECD cell. Thereafter, negative ions are formed in the ion source and are subjected to negative-ion MS/MS/MS in the CID cell. Finally, MS/MS analysis data of positive-ion fragments formed in the ECD cell are acquired, and MS/MS analysis data of negative-ion fragments formed in the CID cell are acquired. An IRMPD cell can be used herein instead of the CID cell, because IRMPD and CID have similar functions. Likewise, an ETD cell can be used instead of the ECD cell, because ECD and ETD have similar functions. This is also true for the following description. CID and IRMPD are examples of adiabatic dissociation, and ECD and ETD are examples of non-adiabatic dissociation.

While the embodiment in FIG. 10 uses an LC/MS instrument, a mass spectrometer in off-line analysis may be controlled in the same manner as above. In this case, however, components subjected to negative-ion analysis may be sequentially subjected to positive-ion analysis.

Figure 12:
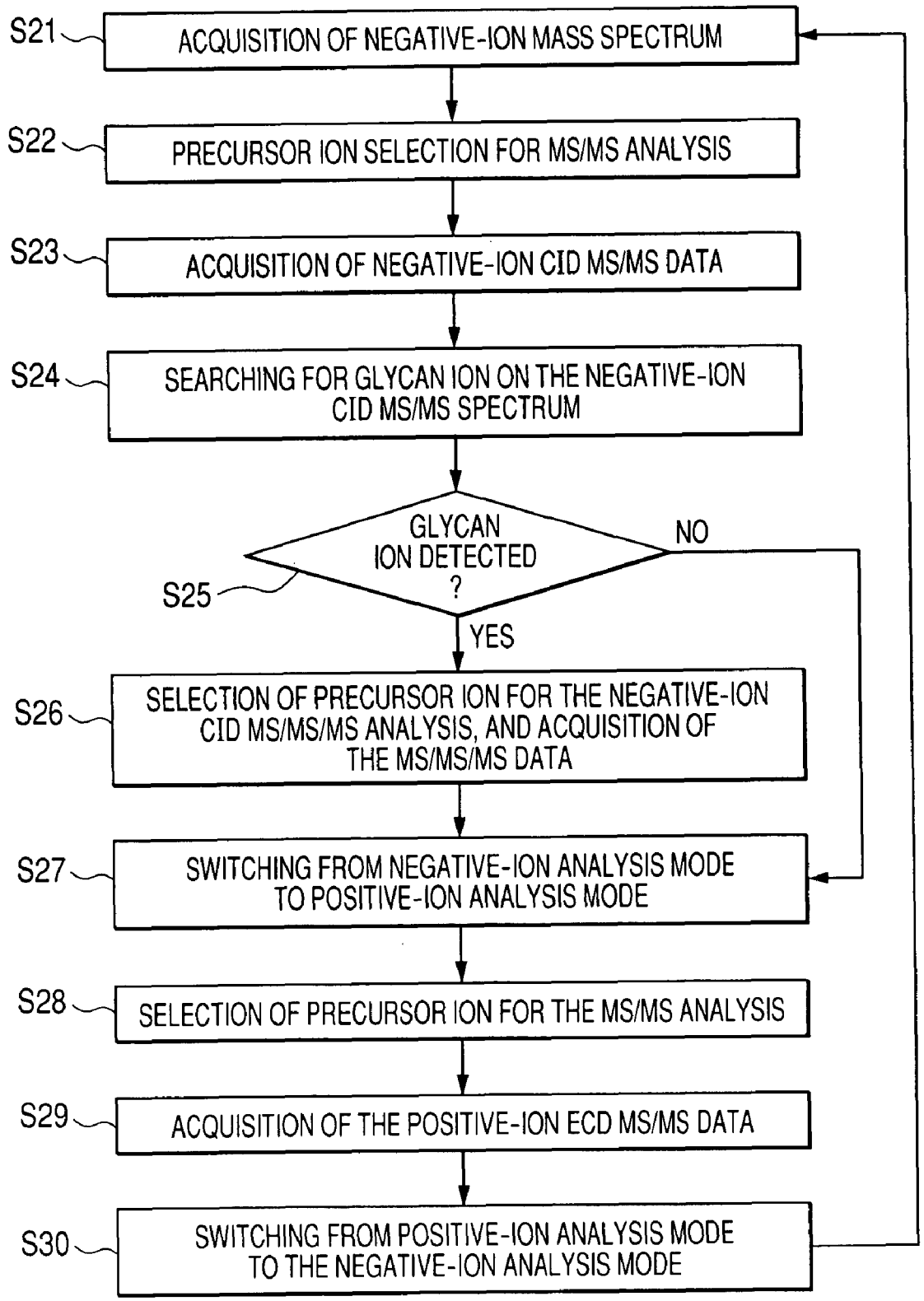
FIG. 12 is a flow chart of MS analysis typically in an LC/MS for use in a method for analyzing glycosylated peptide structures according to another embodiment of the present invention.

FIG. 12 is a flow chart of MS analysis typically in an LC/MS for use in a method for analyzing glycosylated peptide structures according to another embodiment of the present invention. In this embodiment, the positive-ion/negative-ion analysis modes are periodically switched. The analysis is conducted in the following manner. Initially, negative ions are formed and are subjected to mass spectrometry to acquire negative-ion mass spectrometric data (mass spectra) (Step 21). Next, a precursor ion for MS/MS analysis is selected from among the detected ions according to the ion intensity, the charge number, and the range of m/z (Step 22). The selected precursor ion is subjected to CID MS/MS analysis to acquire CID MS/MS analysis data (Step 23). Whether or not a glycan ion is detected in the acquired MS/MS analysis data is determined in real time (Step 24). Specifically, whether or not a singly-charged ion is detected is determined, which singly-charged ion has a m/z agreeing with a value acquired by subtracting the product of the number of glycosidic linkages and 18 from the sum of molecular weights of the monosaccharides, and further subtracting 1 therefrom, or which singly-charged ion has a m/z agreeing with a value further subtracting 18 from the above-mentioned value. If no ion having m/z agreeing with the calculated value is detected in Step 25, the analysis mode of the mass spectrometer is switched from the negative-ion analysis mode to the positive-ion analysis mode after a lapse of a predetermined time, to acquire positive-ion mass spectrometric data (mass spectra) (Step 27). Next, a precursor ion for positive-ion ECD MS/MS analysis corresponding to the precursor ion in the negative-ion MS/MS analysis is selected from among the detected ions (Step 28). If there is no ion satisfying this condition, the procedure is on standby until the analysis mode is returned to the negative-ion analysis mode in Step 30.

If one or more ions having m/z agreeing with the calculated value are detected, an ion having the greatest mass among them is selected as a precursor ion, and the precursor ion is subjected to negative-ion CID MS/MS/MS analysis to acquire negative-ion CID MS/MS/MS analysis data (Step 26). Thereafter, the analysis mode of the mass spectrometer is switched from the negative-ion analysis mode to the positive-ion analysis mode, and positive-ion mass spectrometric data (mass spectra) are acquired (Step 27). A precursor ion for positive-ion ECD MS/MS analysis corresponding to the precursor ion in the negative-ion MS/MS analysis is selected from among the detected ions (Step 28), and MS/MS analysis data of the precursor ion are acquired (Step 29).

Figure 13:
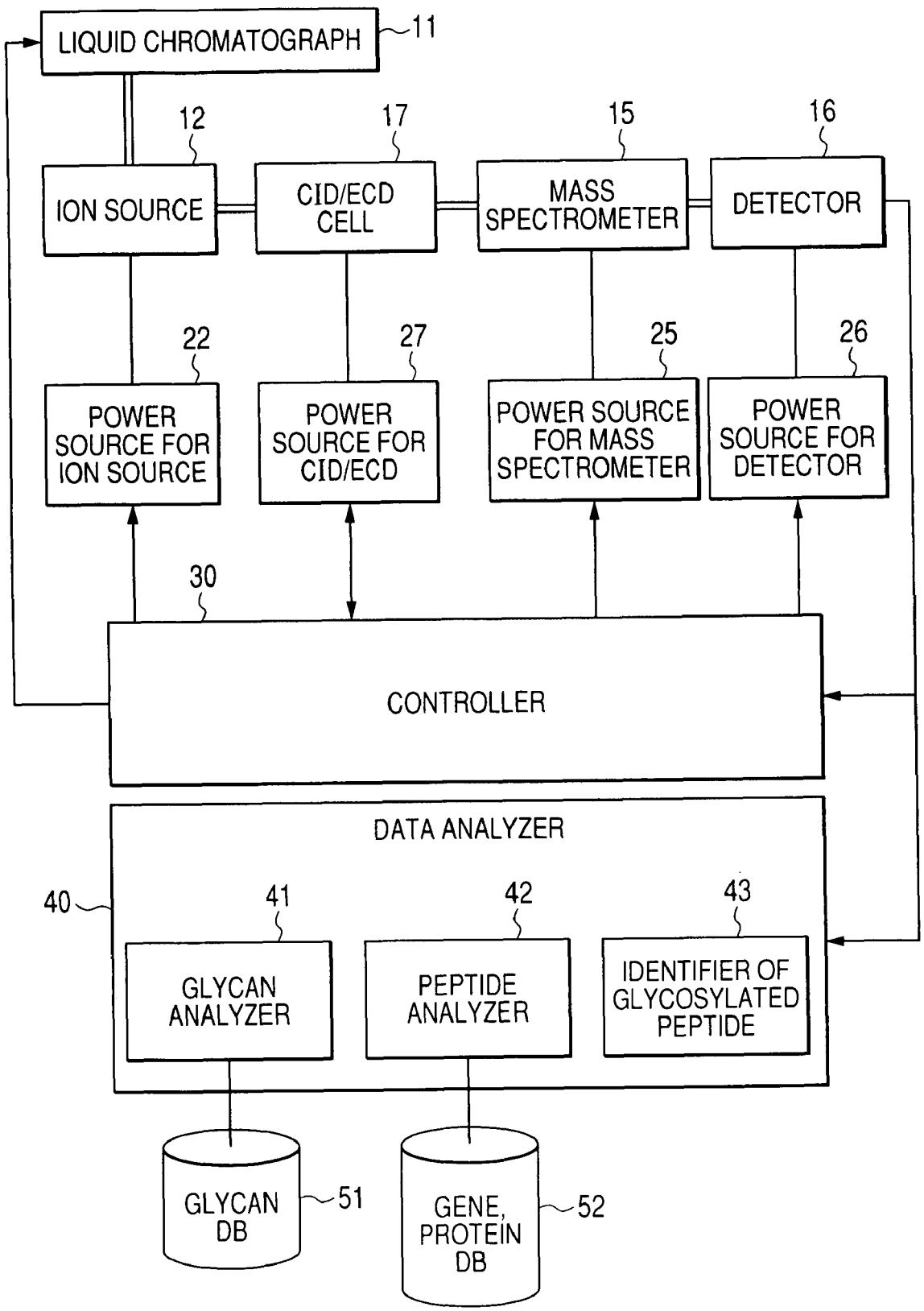
FIG. 13 is a block diagram of an LC/MS for use in a method for analyzing glycosylated peptide structures according to another embodiment of the present invention.

FIG. 13 illustrates a configuration of an instrument in which one device serves both as an ECD cell and a CID cell. As has been described above, a CID/ECD cell 17 structurally having a quadrupole ion trap can theoretically carry out both CID and ECD.

Figure 14:
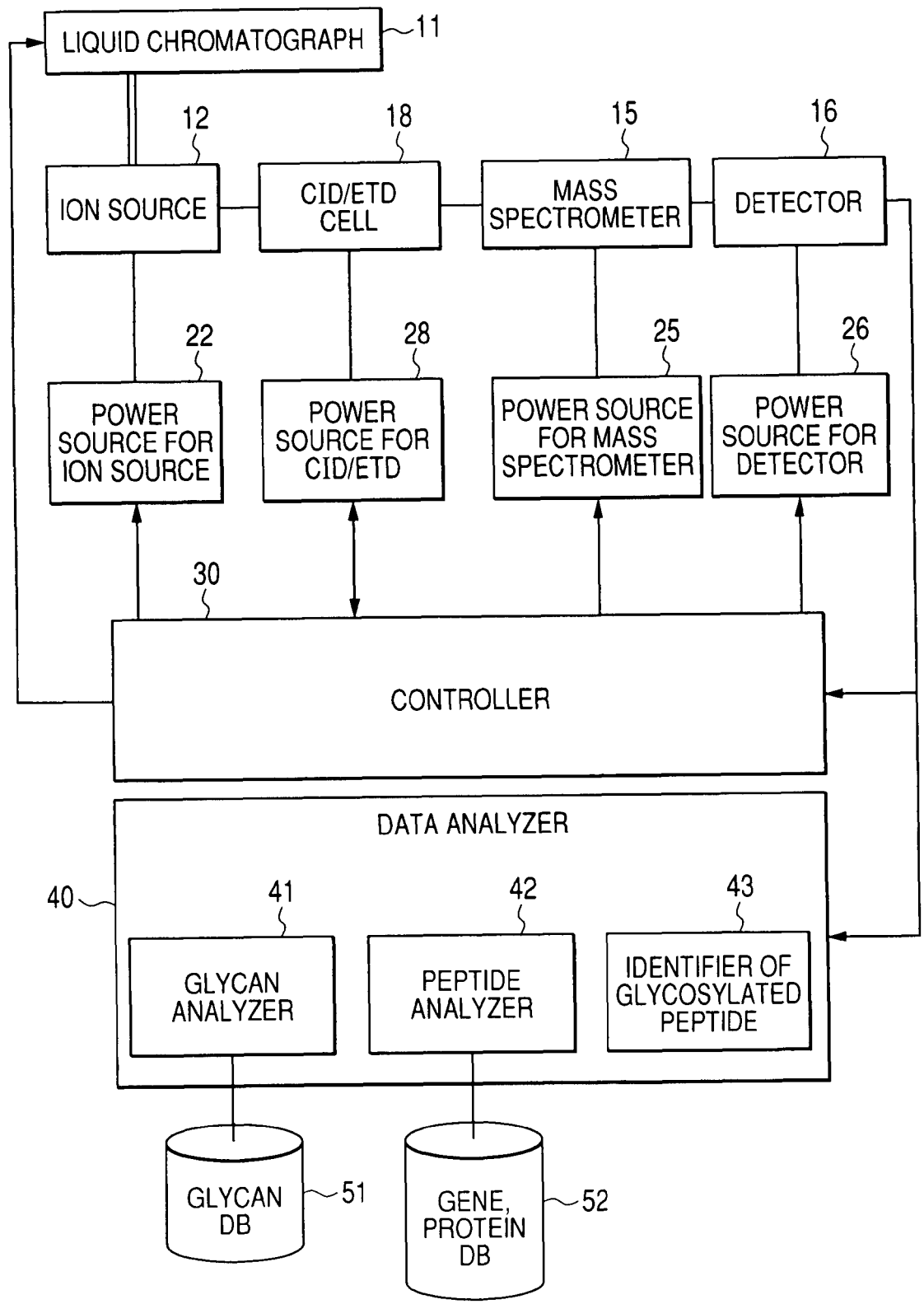
FIG. 14 is a block diagram of an LC/MS for use in a method for analyzing glycosylated peptide structures according to yet another embodiment of the present invention.

FIG. 14 illustrates an embodiment in which a mass spectrometer uses ETD instead of ECD. In this embodiment, a CID/ETD cell 18 is used. According to ECD, positive-ion dissociation occurs as a result of recombining a positive ion with a low-energy electron. According to ETD, a negative ion of a material having a low electron affinity is reacted with a positive ion, and an electron of the negative ion moves to the positive ion, and dissociation occurs in the same process as with ECD. Both ECD and ETD basically carry out a reaction on an ion trapped in a quadrupole ion trap. The mass spectrometers in FIGS. 10, 13, and 14 are arranged independently from a CID or ECD cell. This configuration is employed when the mass spectrometer is a time-of-flight mass spectrometer or a Fourier transform mass spectrometer such as a Fourier transform ion-cyclotron resonance mass spectrometer or an Orbitrap mass spectrometer. When a CID cell or an ECD cell that can conduct mass spectrometry by itself is used, there is no need of arranging an independent mass spectrometer.

What is claimed is:

1. A method for identification of glycosylated proteins and peptides, comprising the steps of:
    ionizing a sample to form negative ions;
    carrying out tandem mass spectrometry of the negative ions through collision-induced dissociation (CID) or infrared multi-photon dissociation (IRMPD) to yield CID or IRMPD mass spectrometric data;
    extracting corresponding glycan information from the CID or IRMPD mass spectrometric data;
    ionizing the sample to form positive ions;
    carrying out tandem mass spectrometry of the positive ions through electron capture dissociation (ECD) or electron transfer dissociation (ETD) to yield ECD or ETD mass spectrometric data;
    extracting corresponding information on a protein or peptide and information on a glycosylation site from the ECD or ETD mass spectrometric data; and
    carrying out identification of the sample based on the extracted glycan information, and the extracted information on the protein or peptide and the extracted information on the glycosylation site.

2. The method according to claim 1, further comprising the steps of:
    retrieving corresponding glycan information from a first database based on the CID or IRMPD mass spectrometric data, the first database including information on spectral patterns derived from glycan structures; and retrieving corresponding information on a protein or peptide and information on a glycosylation site from a second database based on the glycan information extracted from the ECD or ETD mass spectrometric data, the second database including amino-acid sequence information.

3. The method according to claim 1, further comprising the step of analyzing the CID or IRMPD mass spectrometric data to determine whether or not a glycosylated peptide is detected.

4. The method according to claim 1, wherein the step of extracting the glycan information comprises the step of extracting information on candidates about individual glycosylation sites.

5. The method according to claim 1, further comprising the step of separating the sample through normal-phase liquid chromatography.

6. A method for identification of glycosylated proteins and peptides, comprising the steps of:
    acquiring mass spectrometric data of negative ions derived from a sample;
    acquiring mass spectrometry/mass spectrometry (MS/MS) data through CID or IRMPD using, as precursor ions, the detected negative ions;
    determining whether or not at least one glycan ion is detected based on the MS/MS analysis data;
    acquiring negative-ion MS/MS/MS analysis data through CID or IRMPD using, as a precursor ion, a glycan ion having the greatest mass of the detected glycan ions;
    acquiring mass spectrometric data of positive ions derived from the sample;
    acquiring MS/MS analysis data through ECD or ETD of a positive ion corresponding to the precursor ion in the negative-ion MS/MS analysis;
    carrying out identification of the sample based on using mass spectrometric data of both negative ions and positive ions.

7. The method according to claim 6, further comprising the steps of:
    searching a database on known glycans based on the MS/MS/MS analysis data to thereby determine glycan candidates; and searching a protein or gene database based on the positive-ion MS/MS analysis data together with the information on the glycan candidates to thereby identity a protein or peptide in the sample and to determine a glycosylation site of the protein or peptide.

8. An instrument for identification of glycosylated proteins, comprising:

an ion source;

a CID cell or IRMPD cell;

an ECD cell or ETD cell;

a mass spectrometer;

a detector to detect an ion subjected to mass spectrometry by the mass spectrometer;

a controller to control components of the instrument; and a data analyzer to analyze mass spectrometric data detected by the detector, wherein the data analyzer includes:

a glycan analyzer to check the mass spectrometric data against mass spectrometric data of known glycans, a peptide analyzer to check the mass spectrometric data against data of known genes or proteins, and an identifier of glycosylated peptides to combine an output from the glycan analyzer with an output from the peptide analyzer, and wherein the instrument is configured:

to acquire mass spectrometric data of negative ions derived from a sample;

to acquire mass spectrometry/mass spectrometry (MS/MS) data through CID or IRMPD using, as precursor ions, the detected negative ions; to determine whether or not at least one glycan ion is detected based on the MS/MS analysis data;

to acquire negative-ion MS/MS/MS analysis data through CID or IRMPD using, as a precursor ion, a glycan ion having the greatest mass of the detected glycan ions;

to acquire mass spectrometric data of positive ions derived from the sample; and to acquire MS/MS analysis data through ECD or ETD of a positive ion corresponding to the precursor ion in the negative-ion MS/MS analysis.

9. The method according to claim 6, wherein when the glycan ion is note detected based on the MS/MS analysis data, mass spectrometric data of negative ions derived from the sample is acquired again.

10. The method according to claim 6, wherein when the glycan ion is note detected based on the MS/MS analysis data, mass spectrometric data of positive ions derived from the sample is acquired without the MS/MS/MS analysis.

11. The instrument for identification of glycosylated proteins according to claim 8, wherein the CID cell or IRMPD cell and the ECD cell or ETD cell are the same cell device.

* * * * *